US006723049B2

(12) United States Patent
Skladnev et al.

(10) Patent No.: US 6,723,049 B2
(45) Date of Patent: Apr. 20, 2004

(54) APPARATUS FOR TISSUE TYPE RECOGNITION USING MULTIPLE MEASUREMENT TECHNIQUES

(75) Inventors: Victor Nickolaevich Skladnev, Vaucluse (AU); Christopher Kingsley Blunsden, Newport Beach (AU); Rita Stella, Corrimal (AU)

(73) Assignee: Polartechnics Limited (AU)

( * ) Notice: Subject to any disclaimer, the term of this patent is extended or adjusted under 35 U.S.C. 154(b) by 111 days.

(21) Appl. No.: 10/172,703

(22) Filed: Jun. 14, 2002

(65) Prior Publication Data
US 2003/0060696 A1 Mar. 27, 2003

(30) Foreign Application Priority Data
Jun. 15, 2001 (AU) .............................................. PR5718

(51) Int. Cl.[7] ................................................. A61B 8/00
(52) U.S. Cl. ........................ 600/437; 600/407; 600/372
(58) Field of Search ................................ 600/547, 437, 600/426, 407, 372, 373, 382

(56) References Cited
U.S. PATENT DOCUMENTS
5,800,350 A * 9/1998 Coppleson et al. ......... 600/372
6,026,323 A * 2/2000 Skladnev et al. ........... 600/547

* cited by examiner

Primary Examiner—Francis J. Jaworski
Assistant Examiner—Maulin M Patel
(74) Attorney, Agent, or Firm—Gottlieb, Rackman & Reisman, P.C.

(57) ABSTRACT

A method and system are disclosed for recognizing tissue types. Electrical signals are applied to tissue 120 via electrodes 110, 112. Circuitry 106 and the signal processor 116 are used to measure impedance magnitude and phase at a plurality of frequencies. At least the phase information at the plurality of frequencies is compared with phase information of known tissue types. Based on the comparison, the tissue 120 may be assigned to one of the known tissue types.

29 Claims, 6 Drawing Sheets

APPARATUS FOR TISSUE TYPE RECOGNITION USING MULTIPLE MEASUREMENT TECHNIQUES

FIELD OF THE INVENTION

The present invention relates to the recognition of tissue types in human subjects, and, in particular, to such recognition being performed by way of impedance measurements of the electrical properties of tissue.

BACKGROUND

Various arrangements have been described that employ electrical measurements on tissue to derive a diagnosis of the nature of that tissue. Such diagnosis typically relates to the detection of cancerous or pre-cancerous tissue.

For the most part, previous attempts to use electrical measurements for tissue diagnosis have suffered from low performance, as measured by their combined sensitivity and specificity. The measurement of absolute levels of conductivity, for example, has been unreliable through the presence of uncontrolled variability in electrode characteristics. Such variability can occur both over the course of time or between different batches of electrodes.

Previous attempts to use tissue impedance for the detection of cancerous tissue on a patient's surface have not been successful because such have primarily measured the bulk impedance. This has been particularly the case with cervical cancer, which is neoplasia, typically of the upper ten or so cells of the tissue surface being examined.

SUMMARY OF THE INVENTION

It is an object of the present invention to substantially overcome, or at least ameliorate, one or more deficiencies with prior arrangements.

In accordance with one aspect of the present disclosure there is provided a method of tissue-type recognition, said method comprising the steps of:
applying electrical signals to a tissue sample;
measuring from the applied signals a magnitude of impedance of the tissue and corresponding phase sample at each of a plurality of frequencies;
comparing at least the measured phase samples with phase information of known tissue-types taken at said frequencies; and
from said comparison, estimating to which of said known tissue-types said tissue sample corresponds.

In accordance with another aspect of the present disclosure, there is provided a method of tissue-type recognition, said method comprising the steps of:
applying electrical signals to a tissue sample at at least two frequencies from a range of frequencies;
measuring from the applied signals, at each of said at least two frequencies, a magnitude of tissue impedance and a phase of tissue impedance;
calculating a slope of phase versus frequency from said measured phases;
comparing at least said slope with phase slope information of known tissue-types over said range of frequencies; and
from said comparison, estimating which of said known tissue-types said tissue sample corresponds.

In accordance with another aspect of the present disclosure there is provided a method of determining a database for diagnosis of tissue types, said method comprising:

(a) for each of a plurality of tissue samples
   (i) identifying a known tissue type of said sample;
   (ii) taking at least phase measurements using electrical signals applied to said sample, said measurements comprising components at each of a plurality of frequencies.
(b) arranging the phase measurements at each said frequency into a group associated with each said known tissue type.
(c) processing the phase measurements in each said group to provide an processed phase value at each said frequency for each said tissue type.
(d) arranging the average phase measurements as a database.

Other aspects are also disclosed.

The arrangements described herein overcome the problems of making measurements at the tissue surface, whilst avoiding problems that can arise from variability in the surface characteristics of electrodes. These subtle surface characteristics can vary with time, between batches of electrodes and because of contamination by body fluids of the patient, for example due to protein absorption These surface changes can lead to changes in the electrical capacitance of the electrodes measured from the impedance data. Even the mere application of an electrical potential to the electrodes can alter their properties so as to make diagnosis unreliable unless appropriate corrections are made.

BRIEF DESCRIPTION OF THE DRAWINGS

At least one embodiment of the present invention will now be described with reference to the drawings in which.

BEST AND OTHER MODES FOR CARRYING OUT THE INVENTION

Figure 1:
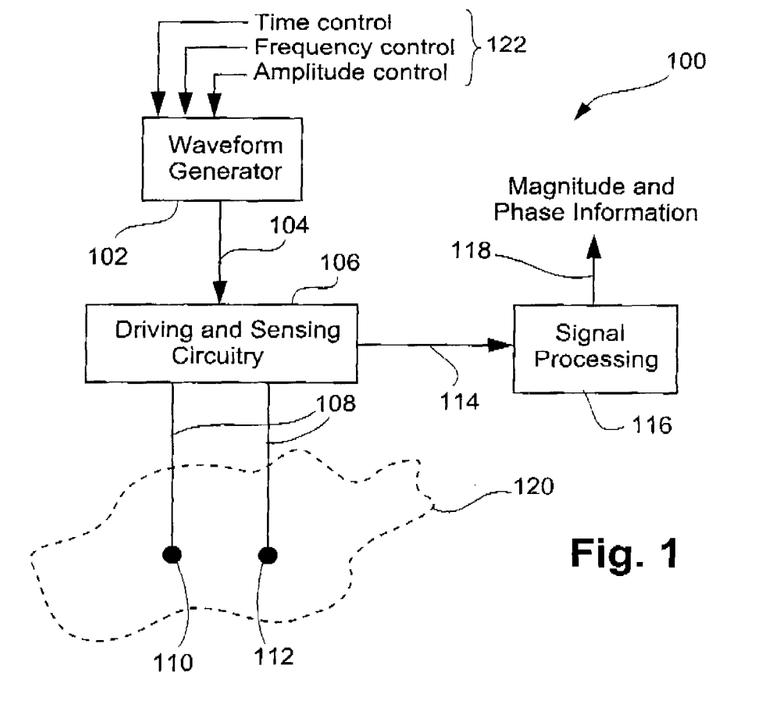
FIG. 1 is a schematic block diagram representation of a tissue type detection system.

FIG. 1 shows a detection system 100 in which waveform generator 102 is used to form signals 104 for use in impedance measurements of the surface of human tissue 120. The waveform generator 102 is preferably controllable independently in terms of each of time, frequency and amplitude by way of control inputs 122. The signals 104 are provided to driving and sensing circuitry 106 which couples the signals to a pair of leads 108, at the ends of which are electrodes 110 and 112 respectively. The electrodes 110, 112 are contacted to the tissue surface 120 in such a fashion that the driving and sensing circuitry 106 can obtain measurements 114 related to the response of the signals 104 in the tissue surface 120. Where multiple pairs of electrodes are used, a multiplexer may be coupled between the electrodes and the driving and sensing circuitry 106 to distribute the stimulus signals and accept the responses from the electrodes. The response signal 114 is then processed in a signal processing arrangement 116 to extract magnitude and phase information 118 relating to the impedance of the tissue surface 120.

Figure 4:
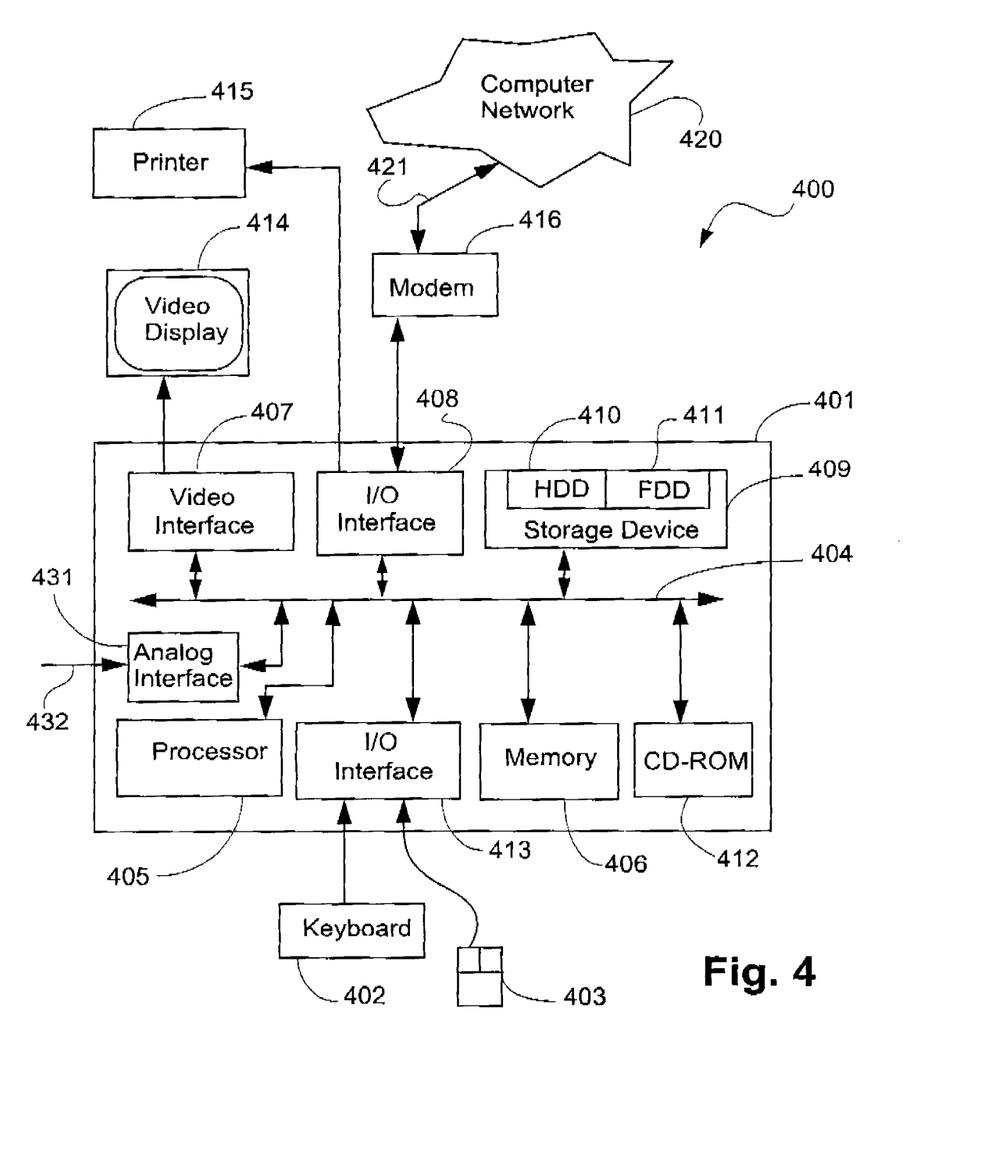
FIG. 4 is a schematic block diagram representation showing detail of an arrangement by which tissue type diagnosis may be performed.

The magnitude and phase information 118 is preferably logged to a computer or microprocessor-based system, such as the system 400 of FIG. 4, for tissue type recognition analysis.

Such analysis of the magnitude and phase information 118 may be implemented using software, such as an application program executing within the computer system 400. In particular, the processing steps may be effected by instructions in the software that are carried out by the computer system 400. The instructions may be formed as one or more code modules, each for performing one or more particular tasks. The software may also be divided into two separate parts, in which a first part performs the tissue recognition methods and a second part manages a user interface between the first part and the user. The software may be stored in a computer readable medium, including the storage devices described below, for example. The software is loaded into the computer system 400 from the computer readable medium, and then executed by the computer. A computer readable medium having such software or computer program recorded on it is a computer program product. The use of the computer program product in the computer system 400 preferably effects an advantageous apparatus for tissue-type recognition.

The computer system 400 is formed by a computer module 401, input devices such as a keyboard 402 and mouse 403, and output devices including a printer 415 and a display device 414. A Modulator-Demodulator (Modem) transceiver device 416 is used by the computer module 401 for communicating to and from a communications network 420, for example connectable via a telephone line 421 or other functional medium. The modem 416 can be used to obtain access to the Internet, and other network systems, such as a Local Area Network (LAN) or a Wide Area Network (WAN), The computer module 401 typically includes at least one processor unit 405, a memory unit 406, for example formed from semiconductor random access memory (RAM) and read only memory (ROM), input/output (I/O) interfaces including a video interface 407, and an I/O interface 413 for the keyboard 402 and mouse 403, and an interface 408 for the modem 416. A storage device 409 is provided and typically includes a bard disk dive 410 and a floppy disk drive 411. A magnetic tape drive (not illustrated) may also be used. A CD-ROM drive 412 is typically provided as a non-volatile source of data. The components 405 to 413 of the computer module 401 typically communicate via an interconnected bus 404 and in a manner which results in a conventional mode of operation of the computer system 400 known to those in the relevant art. Examples of computer systems on which the described arrangements can be practised include IBM-PC's and compatibles, Sun Sparcstations or alike computer systems evolved therefrom. Other computers may also be used.

Typically, the application program is resident on the hard disk drive 410 and read and controlled in its execution by the processor 405. Intermediate storage of the program and any data fetched from the network 420 may be accomplished using the semiconductor memory 406, possibly in concert with the hard disk drive 410. In some instances, the application program may be supplied to the user encoded on a CD-ROM or floppy disk and read via the corresponding drive 412 or 411, or alternatively may be read by the user from the network 420 via the modem device 416. Still further, the software can also be loaded into the computer system 400 from other computer readable media. The term "computer readable medium" as used herein refers to any storage or transmission medium that participates in providing instructions and/or data to the computer system 400 for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external of the computer module 401. Examples of transmission media include radio or infra-red transmission channels as well as a network connection to another computer or networked device, and the Internet or Intranets including e-mail transmissions and information recorded on Websites and the like.

The tissue-type recognition processes may alternatively be implemented in dedicated hardware such as one or more integrated circuits performing appropriate functions or sub functions. Such dedicated hardware may include graphic processors, digital signal processors, or one or more microprocessors and associated memories.

The magnitude and phase information 118 may be supplied to the computer system 400 by way of the computer network 420, where the signal processing arrangement 116 has capacity to provide an appropriate output to such a network. Alternatively, the signal processing arrangement 116 may couple to an analogue interface 431 of the computer module 401 where the magnitude and phase information 118 is provided to an input 432 of the interface 431. The analogue interface 431 may then operate to convert the magnitude and phase information 118 into a digital form able to be processed by the computer module 401. The presentation of the magnitude and phase information 118 to the computer module 401 provides for storage of the raw measured data using the storage device 409 and also for the processing of that information and the storage of subsequent processed results.

In operation, the electrodes 110 and 112 are positioned on the tissue 120, and the electrical impedance and phase response are then determined over a range of frequencies established by the waveform generator 102. A multiplexer again may be used where multiple pairs of electrodes are used. From this data, the values of equivalent resistance and capacitance of the electrode system formed by the leads 108, electrodes 110 and 112, and tissue 120, can be determined. This data is obtained using established electronic techniques.

The electrode system incorporating the leads 108, and electrodes 110 and 112 is formed by an arrangement of bipolar electrodes in which the same electrodes that are used to apply energy to the tissue 120 are also used to measure the impedance of the tissue 120. Such an arrangement is used to focus on the influence of the tissue surface layers on the data that is gathered, as compared to the response of the electrodes themselves, which may be considered complementary for each of application and sensing.

As an example, it has been found that impedance measurements of cervical tissue are able, on average, to distinguish amongst many different tissue types that can be present. Considering the dominant cervical tissue types, squamous tissue has a high impedance, whereas columnar has low impedance, and cancerous tissue is of mid-range impedance. Unfortunately, the spread in these measurements is such as to render the technique of merely determining impedance as having no value as a screening tool for cervical cancer. Such has been verified by a number of independent sources.

Careful study of the magnitude and phase information 118 by the present inventors has shown that the slope of the phase of the impedance data versus frequency varies with tissue type. This data can be used to lessen the reliance on the simple magnitude of the impedance, which is not sufficiently reliable for recognition purposes particularly due to changes in electrode properties, such as electrode capacitance. Various electrode configurations and spacings may be used to obtain more information regarding the impedance at varying tissue type depths.

Figure 2A:
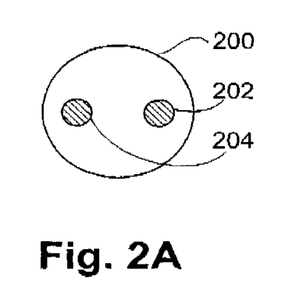
FIGS. 2A to 2D depict various probe arrangements each incorporating plural electrodes.

A preferred implementation of the electrode assembly incorporating the leads 108 and electrodes 110 and 112 comprises a probe arrangement specifically configured for the detection of cervical cancers. Such a probe may be sized and shaped similar to a writing pen and is configured with the electrode arranged at the tip of the probe whereby the probe may be moved to engage the surface of the cervix in an attempt to detect pre-cancerous and cancerous tissue. FIG. 2A shows a simple probe tip 200 of such a device in which a pair of electrodes 202 and 204 are arranged. As seen, the electrodes 202 and 204 are each circular in shape and are typically spaced apart by approximately 2 mm, thereby giving the probe tip 200 as having an overall diameter of approximately 5–7 mm.

Figure 2B:
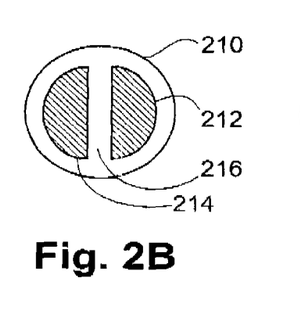

An alternate arrangement is shown in FIG. 28 where a probe tip 210 includes two semi-circular shape electrodes 212 and 214 which are separated by a distance 216, again of approximately 2 mm. Such an arrangement provides that conduction between the electrodes 212 and 214 occurs in the surface layers of the tissue 120, rather than in the bulk of the tissue 120.

Figure 2C:
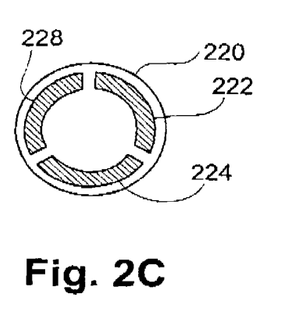

An further alternate arrangement is shown in FIG. 2C which incorporates a three electrode configuration that is also operable in the "bipolar" manner described above. In FIG. 2C, an electrode tip 220 is shown having three electrodes 222, 224 and 228 each occupying approximately one third of an arc of an annulus defined substantially by the diameter of the probe tip 220. With such a configuration, any two of the electrodes 222, 224 and 228 or paired combination such as one electrode with respect to the other two electrodes, may be used to provide and detect a stimulus. Further, samples may be made by alternating the reference electrode thereby providing for each of the electrodes 222, 224 and 228 to be used as each of a driving electrode and for a different sample, a reference electrode.

Figure 2D:
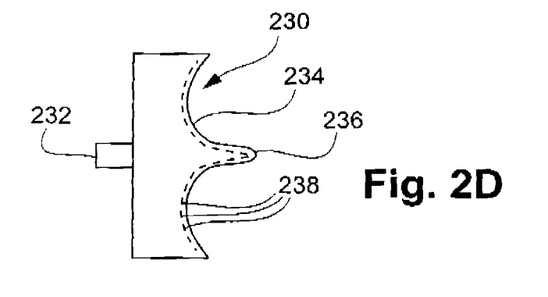

FIG. 2D shows a transverse cross sectional representation of a further electrode tip 230 specifically adapted for detecting cervical cancers. The probe tip 230 includes a mounting portion 232 by which a coupling wand may be connected to convey electrode leads and to provide for resilience support as the probe 230 is engaged with the cervix. Specifically, the probe includes a tip having a circular surface having a concave portion 234 formed as an annulus about a central elongate portion 236. With such a configuration, the probe tip 230 may be engaged with the cervix such that the central extension 236 may enter the birth canal to enable detection of pre-cancerous and cancerous tissues within the birth canal which would not ordinarily be detected by exterior probing. Arranged across the curved surface of the probe tip 230 that engages the cervix are a number of electrodes 238 arranged in a fashion corresponding to or similar to the electrodes of FIG. 2A, and which may be activated and sensed in a bipolar sequence to obtain impedance measurements from various portions of the cervical surface.

Figure 2E:
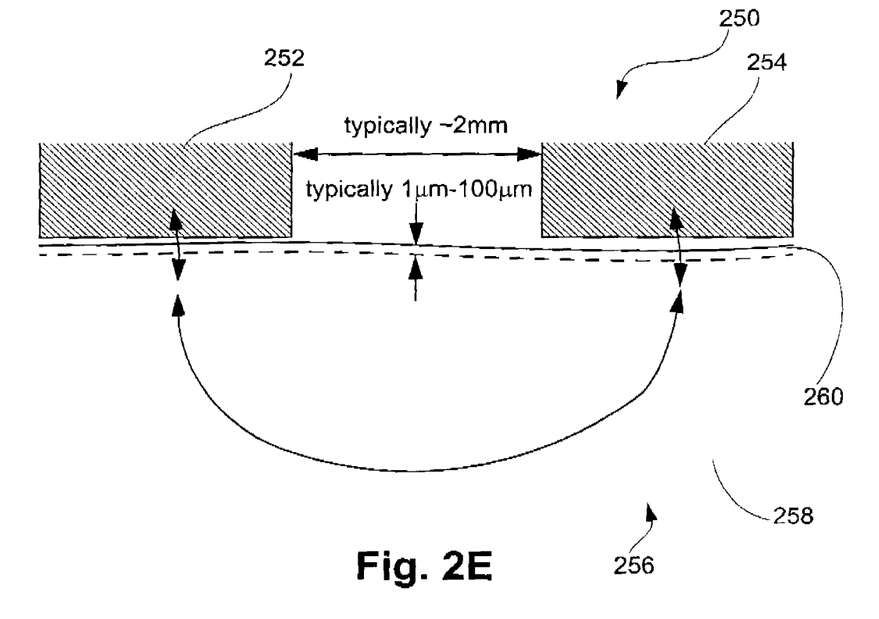
FIG. 2E is a cross sectional representation showing the conduction paths between a pair of electrodes when contacted to tissue.

FIG. 2E schematically illustrates the typical conduction process performed in the impedance measurements described herein. In FIG. 2E an arrangement 250 of electrodes 252 and 254 are contacted against a patient's tissue 256. The tissue 256 may be construed as having a surface component 260 and a bulk component 258. Importantly, the surface component 260 can vary in size from about 1 micrometer (ie. that of only a few tissue cells), up to something like about 100 micrometers. With an electrode spacing of approximately 2 mm as illustrated, the surface component 260 thus represents a very small boundary between the electrodes 252 and 254, and the bulk tissue 258. In the present arrangements, and for the detection of many pre-cancers and cancerous tissues, particularly in cervical tissues, it is the response of the surface portion 260 that is important, and not that of the bulk tissue type 258. As a consequence, the form of interaction between the electrodes 252 and 254 and the surface 260 substantially influences the reliability of measurements obtained and, as a consequence, the determination of any tissue types detected.

The electrode configurations that may be used depend upon the form of tissue being diagnosed. For example, with cervical tissue, the above described arrangements may be used. This allows the electrodes to be placed upon the cervix through an aperture provided by a speculum that is used to open the vagina. Other electrode configurations may also be used.

Where the examination is to be done on the walls of tubular organs such as those of the endocervical canal, the electrodes are usually positioned on the outer wall of a cylindrical probe. Pressure is exerted during use of the probe to ensure that the electrodes make adequate contact with the walls. Other configurations may be used.

As indicated above measuring circuit employed may comprise the measurement of the electrical properties between pairs or groups of electrodes. Other configurations may entail measurement between one electrode and several others that are in contact with the tissue being measured. In other cases, a separate reference electrode may be placed on the patient in a convenient area and measurements made between the reference electrode and other electrodes that are in the tissue being diagnosed. The size and spacing of electrodes will have effects with regards to the bulk tissue impedance measured. In this regard, the current from large, widely spaced electrodes is more likely to follow a path through deeper (low impedance) tissue, such as the tissue 258, than would the source current from small, closely spaced electrodes.

The material of the electrodes can be metallic or some other conductor such as conductive polymers. The surface electrode chemistry of the electrodes needs to be predictable so that reproducible data is obtained on the various tissue types. The composition of the electrodes must be such as to not present dangers to the patient. Some metals and polymers may lead to irritation of the tissue and thus need to be avoided. Suitable biocompatible materials are generally available. Gold satisfies these requirements and is a preferred material for the electrodes described above.

The signal processing arrangement 116 can be implemented using an impedance spectrum analyser widely available in the art. The system 100, as with other medical devices must provide for electrical safety for the patient. Isolation circuitry is thus necessary in each of the components of the system 100 until a stage can be configured whereby patient isolation and safety can be ensured.

Data from the system 100 is typically analysed by a computer since the relationship between any one measured parameter and the type or health of the tissue is not simple. The general purpose computer configuration of FIG. 4 thus may be used. The computer for system 400 is interfaced with the spectrum analyser (forming the signal processing arrangement 116) to thereby provide an output via the video display 414 or printer 415 to inform a user of the results of the impedance computations. As an alternative to use of a general-purpose computer system 400, a stand-alone digital signal processing (DSP) system having a corresponding operable functionality, may be used.

Algorithms used by the computer 400 for assessing the magnitude and phase information 118 are derived from data gathered using the same or equivalent devices for measuring tissue. That data is extracted from known tissue types and is gathered and used to derive suitable equations to provide the various diagnoses. The diagnoses that are used to characterise the type or health of the tissue may be one of several or may be combinations of methods. In the case of cervical tissue, the available methods of diagnosis includes cytology, hystology, and colposcopy, which often do not agree with each other. Similar ranges of tools are available for other tissue groupings. Further, the various methods of diagnoses described herein may become part of a broader repertoire of methods of tissue analysis given that such do not require intervention of a human interpreter to arrive at results.

The present inventors have found that the phase data can be employed to underpin the impedance data and to significantly raise the reliability of the diagnosis. It has been found by the present inventors that over the frequency range of 200 Hz to 200,000 Hz, the phase response when using gold electrodes of area 2 square millimeters, distinguishes reliably amongst the three dominant tissue types. At mid-range (on a logarithmic scale) frequencies, the phase response are as follows:

squamous tissue: phase rising with frequency
columnar tissue: phase falling with frequency
cancerous tissue: phase relatively unvarying with frequency.

EXAMPLE 1

A particular application of the present disclosure for the diagnosis of cervical abnormalities can be described as follows. An arrangement of electrodes according to FIG. 2C, each having an area of 2 mm$^2$, was applied to the surface of the cervix and the magnitude of the impedance was measured together with the phase of impedance at each of two frequencies. The tissue types displayed parameters according to Table 1 below:

TABLE 1

| Tissue Type | Magnitude of Impedance at 5 kHz | Magnitude of Impedance at 10 kHz | Ratio of phases 5 kHz/10 kHz |
| --- | --- | --- | --- |
| Squamous | 7000 | 5000 | 0.88 |
| Pre-cancerous | 2000 | 1700 | 1 |
| Columnar | 800 | 700 | 1.25 |

It was observed by the present inventors that the phase ratios indicated in Table 1 remain substantially constant even if the electrode capacitance is changed by significant amounts, such as ±20%. This was because the phase was measured in a region of constant phase slope for each tissue type. This region extends beyond the measurement points by at least 20% in frequency. A change in electrode capacitance caused by protein absorption only shifted the frequency axis and did not change the slope of the phase in the range specified. Hence, the present inventors determined that it is important to choose measuring frequencies at which the slope of the phase is substantially constant, for the calculation of the phase ratio.

EXAMPLE 2

A larger sampling of tissue types over a broader range of frequencies was obtained, the results of which are found in Table 2 and Table 3 arranged at the end of this description and before the accompanying claims. The values indicated in Table 2 and Table 3 represent average values obtained from samples taken from 50 examples of each normal tissue type, and the cancerous tissue from 5 patients. Thus the values provide a statistically reliable basis for the results derived therefrom. Those results are also plotted in FIGS. 3A and 3B. In this example, the "calibration" tissue is a standard medical grade saline solution. From FIG. 3A, it will be appreciated that for each tissue type depicted, the magnitude of impedance declines over the frequency range in question. It is further noted that high grade cancerous tissue has an impedance magnitude lying between the typical cervical tissue types such as columnar and squamous, both of which are normal tissue types. In this regard, columnar tissue is mucosal and in many respects is representative of or associated with bodily fluids encountered in the cervical region. Squamous tissue on the other hand is substantially skin-like. Each of these are normal tissue types and quite distinct from high grade cancerous tissue.

Figure 3A:
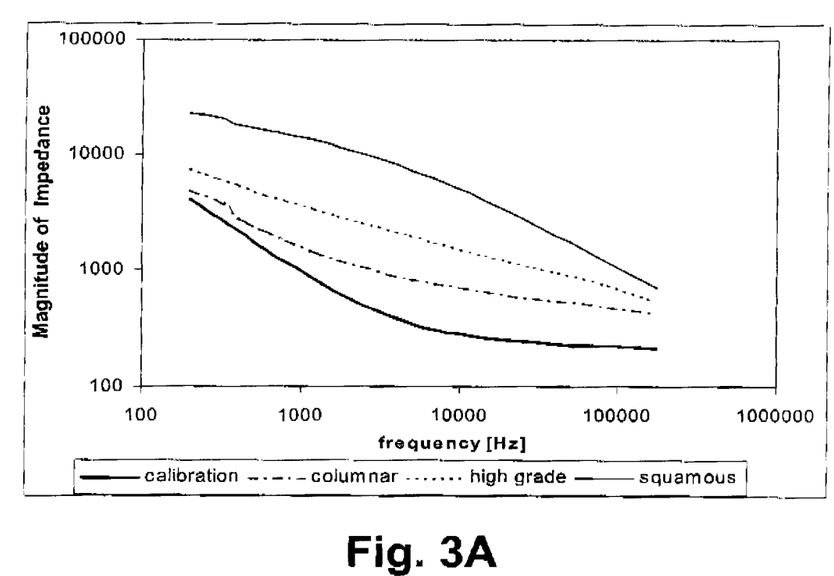
FIG. 3A is a plot of the impedance magnitude for a range of frequencies and tissue types using the arrangements of FIGS. 1 and 2C.

Considered in isolation, the magnitude of impedance plot of FIG. 3A, whilst statistically showing that cancerous tissue is distinct from the others in the trial, was not considered, of itself, to be sufficiently authoritative to form the basis of a diagnosis of tissue recognition due to the effect of varying electrode capacitance.

Figure 3B:
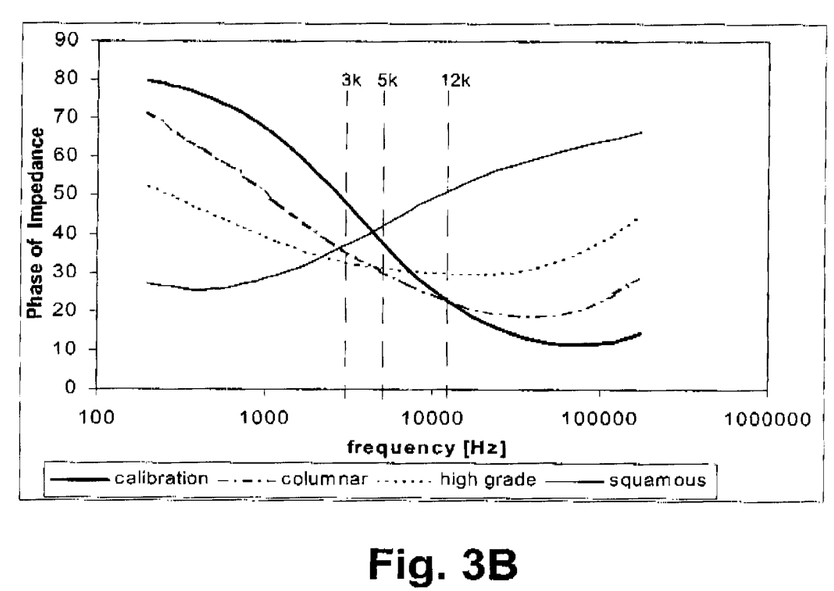
FIG. 3B is a plot of phase characteristics associated with the impedance characteristics of FIG. 3A.

However, observing the plot of impedance phase shown in FIG. 3B, the present inventors realised that the different tissue types displayed substantially different phase characteristics over the measured frequency range, Consistent with Example 1, both normal tissue types (columnar and squamous), together with the calibration type, displayed significant and substantially constant slope during the midrange frequency band (ie. 5 kHz to 10 kHz). Squamous tissue displayed a slope having a different sign to that of columnar and calibration tissues. Of significance is the phase plot for high grade cancerous tissue which is seen to have a decreasing phase at low frequencies, an increasing phase at higher frequencies, and a substantially constant or level phase plot during the mid band frequencies. The substantially flat portion of the high grade cancerous phase plot contrasts each of the other phase plots within that frequency band. It is this distinct relationship between the phase plot of high grade cancerous tissues against the phase plots of normal tissues that provide a distinguishing feature enabling the diagnosis of high grade pre-cancerous and cancerous tissues based upon impedance measurements utilising phase.

Further, multiple types of measurements may be additionally used to improve the discrimination between tissue-types. For example, absolute magnitude and phase may be combined with other variables. Also, whereas the data shown in FIGS. 3A and 3B represent averages taken over the respective samples, other forms of processing may be used to determine useful reference magnitudes and phase of impedance for tissue types and certain frequencies. For example, curve fitting may be applied to best match a spread of sample data.

It will be further observed that the impedances fall into a pattern that is related to the mucosal qualities of the tissue. Although the phase changes in slope from negative to positive, the pre-cancerous tissue shows a fairly constant phase over the frequency range of interest. Whilst the average values of the impedance magnitude of FIG. 3A of all of these quantities is diagnostic, such values can vary considerably in that they possess a relatively large amount of noise. A consideration of both magnitude and phase provides, according to the present disclosure, for a minimisation in errors in diagnoses.

Errors in measurements can be ameliorated by the taking of multiple impedance samples at each of the various frequencies prior to obtaining an average value for that frequency. At least two frequencies such as 5 kHz and 10 kHz should be used, although measurements over the broader range, as illustrated in FIGS. 3A and 3B provide for substantial improvements in accuracy. As seen from FIG. 3B, frequencies in the band from about 3 kHz to about 12 kHz characterise substantially linear portions of each of the phase plots. For a detailed result, a swept continuous frequency may be used enabling the accurate plotting of the phase change over swept frequency range, as illustrated in FIGS. 3A and 3B. It is to be noted that the frequencies used in FIGS. 3A and 3B are statistically applicable to cervical cancers and that other frequency bands or specific frequencies may be shown to be diagnostic for other types of tissue. An advantage in measuring at only a few (eg. 2) frequencies is that such measurements are faster, and can be processed faster, thereby enabling measurements from multiple electrode pairs within an acceptable time frame.

Figure 3C:
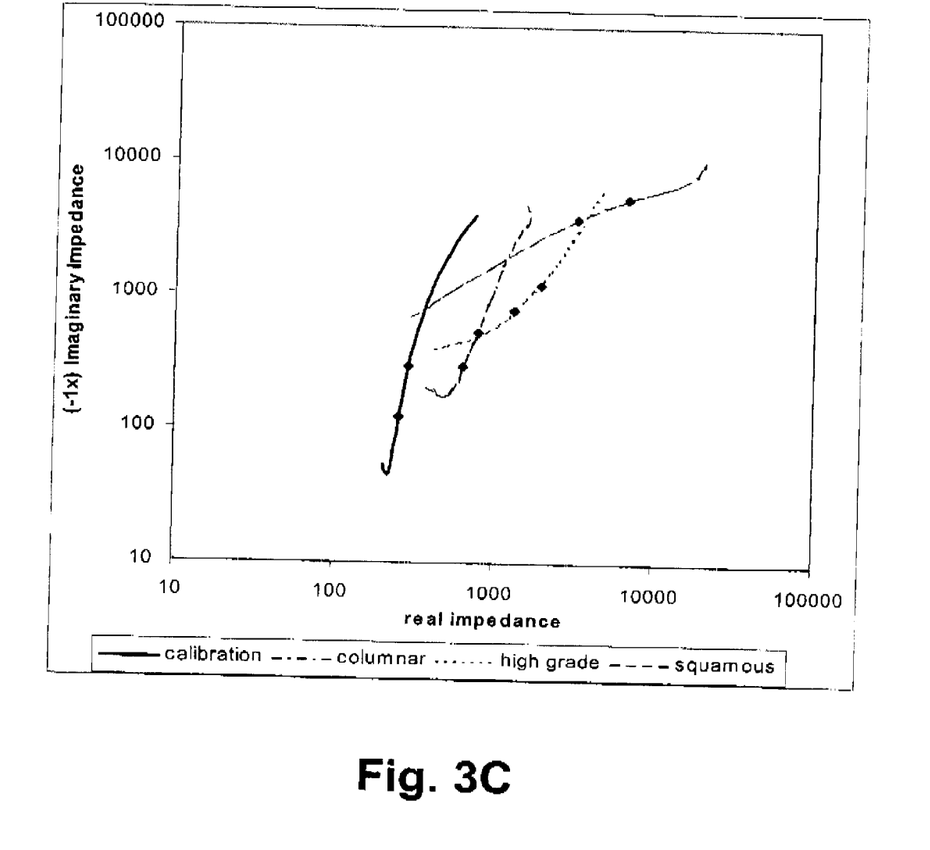
FIG. 3C is a plot of the real and imaginary parts of impedance calculated from the data of FIGS. 3A and 3B.

FIG. 3C shows a plot of the real and imaginary parts of the complex impedance determined from the sample data of Table 2 and Table 3, used to construct the plots of FIGS. 3A and 3B. The plots of FIG. 3C include markers on each trace to indicate the frequency band of 3.5 kHz to 10 kHz. This alternative view of the impedance data also holds possibilities for tissue-type discrimination. The sections of the curves in the 3.5–10 kHz range display different gradient and spatial characteristics.

The arrangement described, through optimal selection of electrodes, overcomes problems of electrode variability. In this regard, FIG. 3A in respect of the calibration "tissue" (ie. saline solution), is highly indicative of the capacitive effects of the electrodes whereby the impedance declines progressively with frequency. At higher frequencies, the resistance dominates the impedance and thus the magnitude stops decreasing with frequency. This is seen from the calibration curve in FIG. 3A to occur at approximately 8 kHz where there is an apparent change in slope of the curve. At lower frequencies (eg. 300 Hz–1 kHz) the measured impedance is affected by the capacitive effects of the electrodes.

The measurements of impedance noted above may be obtained using a constant amplitude stimulus signal 104. The arrangements may be further enhanced by measuring the pulse response of the tissue in order to determine frequency and phase components in response to pulses. In such an implementation, by adjusting the time control input 122, the waveform generator 102 may output a series of pulses. Measurements using a time-domain or pulse response are described in U.S. Pat. Nos. 5,800,350 and 6,026,323. Using measurements made via a pulse technique enables the system 100 to characterise the electrodes so that corrections may be made to measured impedance data. In the same manner, measurements made using a spectrum analyser approach described above can be used to improve the quality of the pulse data. Such further reduces uncertainties in respect of the diagnosis.

In addition to the application of a constant amplitude signal, the time domain approach as described in U.S. Pat. No. 5,800,350 involves stimulating the tissue with a voltage pulse and measuring the current flowing into the patient during the pulse and the decay of the tissue voltage after the pulse. This technique is sensitive to variations in the parametric performance of the electrodes and time domain analysis techniques discussed below have been developed to reduce the effect of the electrode parametric variation.

The time domain technique involves using the time constants of the end of the current and voltage curve to obtain an estimate for the electrode capacitance. This estimate can then be used to correct for variations in the decay curves due to electrode capacitance variations. In the apparatus from which the experimental results of Tables 2 and 3 were obtained, a time constant of 200 $\mu s$ was found and resulted from the electrode size, and the probe input impedance.

Figure 5A:
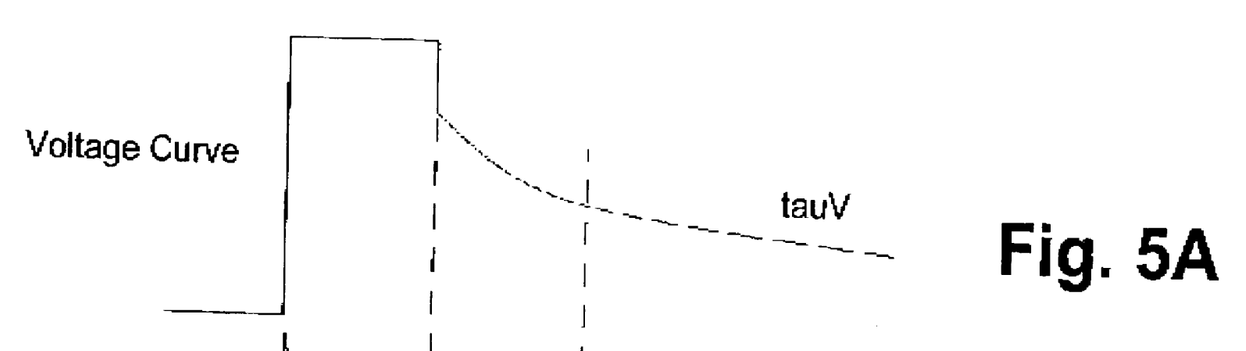
FIG. 5A is a plot a voltage stimulus and response.
Figure 5B:
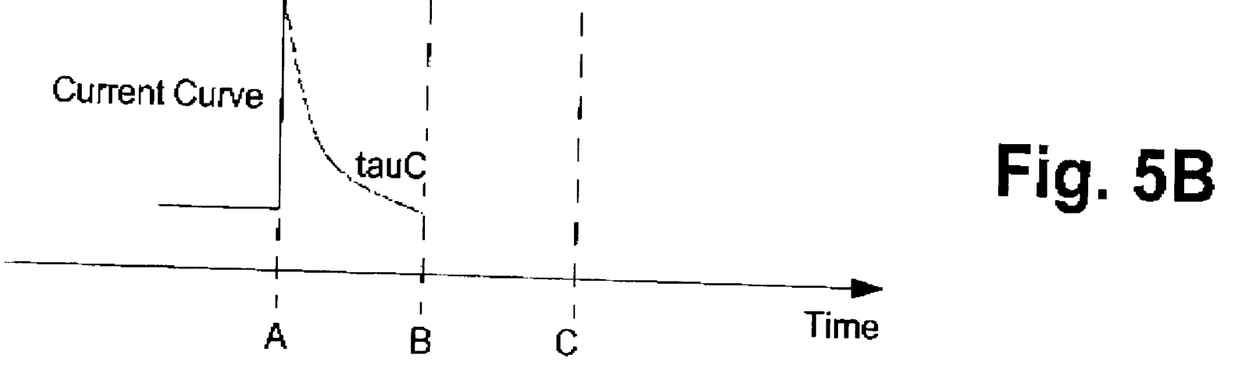
FIG. 5B is a plot of a corresponding current stimulus and response.

FIGS. 5A and 5B show a voltage curve and current curve respectively. Application of the voltage pulse leads to current flowing into the patient. Initially the current curve is dominated by current charging up the tissue capacitance. However the tail of the current curve is dominated by residual charging of the electrodes through the resistance of the patient. Likewise, after the pulse, the voltage curve decays with the initial 200 $\mu s$ of the curve affected by the tissue capacitance and electrode capacitance. By the tail of the voltage curve (after 200 $\mu s$ for our electrodes and input resistance) the decay time constant is dominated by the electrode capacitance. Thus the decay displays a double-layer effect influenced by two capacitances.

The time constant (tau) of the tail of the current and voltage curves (tauC and tauV as seen in FIGS. 5A and 5B) can be calculated from the slope of the curves using Equations 1 below:

$$tauC = \frac{-Itail}{\frac{dItail}{dt}} \quad tauV = \frac{-Vtail}{\frac{dVtail}{dt}} \quad \text{Eqn. (1)}$$

The time constants can then be used to estimate the electrode capacitance (CE) using Equation 2, where Rin is the input resistance of the measurement device (typically around 10 k$\Omega$):

$$CE = \frac{tauV - tauC}{Rin} \quad \text{Eqn. (2)}$$

The electrode capacitance calculated in this way has shown to be sensitive to production variation in the electrodes, while at the same time retaining some residual tissue discrimination due to its sensitivity to the surface of the tissue. Hence techniques were developed to normalise out (ie. nullify) production variation while at the same time retaining the tissue discrimination. This was done by performing measurements in standard saline solution prior to measurements on tissue and using the electrode capacitance calculated from the saline measurements to derive a correction factor for the tissue decay curves.

The electrode capacitance (CEsaline) measured on the standard saline solution (ie. the calibration "tissue") is compared with a target value (CEtarget), and a correction factor is calculated using Equation 3:

$$norm = \frac{CEsaline}{CEtarget} \qquad \text{Eqn. (3)}$$

The values of the voltage decay curve can then be normalised, according to Equation 4:

$$Vdecay\_norm(t) = Vamp\_norm\left(\frac{Vdecay(t)}{Vdecay(tref)}\right)^{norm} \qquad \text{Eqn. (4)}$$

where Vamp_norm is calculated be comparing the decay curve amplitude measured using test solution and the target reading at t=tref using sensitivity analysis techniques known to those skilled in the art. The amplitude normalisation time point (tref) is chosen to occur after the decay in the tissue response has reached zero but before the electrodes have fully decayed. This is around 300 µs in the system described herein.

The above techniques were developed assuming the current and voltage curve decays follow pure exponentials (ie. the electrode impedance is a linear capacitance). In practice, the electrode impedance can be modelled as a constant phase element with impedance given by Equation (5) below:

$$ZE = \frac{1}{CE \times s^\alpha} \qquad \text{Eqn. (5)}$$

In Equation 5, α determines the distribution of time constants in the voltage decay waveform. For a linear capacitor, α is equal to one and there is only one time constant which is constant during the voltage decay. For other values of α, the effective time constant increases with time during the voltage decay.

The techniques derived for exponential decays can be applied to the case where the electrode impedance is a constant phase element by calculating a time constant and correction factor for each point in the decay curve. The assumption of an exponential decay with constant time constant is valid over small time steps. This is depicted in Equations 6, 7 and 8 below:

$$tau(t) = \frac{-Vdecay(t)}{dVdecay(t)/dt} = \frac{-Vdecay(t)}{Vdecay\left(t+\frac{\Delta t}{2}\right) - Vdecay\left(t-\frac{\Delta t}{2}\right)} \times \Delta t \qquad \text{Eqn. (6)}$$

$$norm(t) = \frac{\tau_{saline}(t)}{\tau_{target}(t)} \times \frac{\alpha_{saline}}{\alpha_{target}} \qquad \text{Eqn. (7)}$$

$$Vdecay\_norm(t) = Vamp\_norm\left(\frac{Vdecay(t)}{Vdecay(tref)}\right)^{norm} \qquad \text{Eqn. (8)}$$

where Vamp_norm and tref are as previously defined.

The value for α can be measured using impedance sweep data using techniques known to those skilled in the art. In this fashion, an impedance measured using the swept frequency technique can be used to provide correction factors for the time domain analysis.

Further accuracy in diagnosis can be obtained through combining the impedance measurements with measurements of other tissue parameters such as optical properties, also described in the above noted U.S. patents.

The present inventors have determined that this technique will substantially and reliably remove the effect of the production variation in the decay curves while at the same time retain the tissue discrimination provided by the electrode capacitance measured on the tissue. The measurements in saline can occur either during production test or just prior to electrode use.

The foregoing describes only a number of embodiments of the present invention and modifications can be made thereto without departing from the scope of the present invention. AUSTRALIA ONLY In the context of this specification, the word "comprising" means "including principally but not necessarily solely" or "having" or "including" and not "consisting only of". Variations of the word comprising, such as "comprise" and "comprises" have corresponding meanings.

TABLE 2

| | Magnitude of Impedance (ohms) | | | |
|---|---|---|---|---|
| Freq (Hz) | Calibration | Columnar | High Grade | Squamous |
| 200 | 4046.27 | 4840.66 | 7487.40 | 22271.23 |
| 300 | 2793.38 | 3928.01 | 6179.43 | 20601.38 |
| 400 | 2154.84 | 2838.01 | 5354.78 | 17770.10 |
| 600 | 1504.18 | 2142.37 | 4434.73 | 15986.29 |
| 800 | 1173.60 | 1797.53 | 3973.85 | 14705.42 |
| 1200 | 841.05 | 1448.91 | 3392.03 | 13068.83 |
| 1700 | 645.85 | 1236.82 | 2975.88 | 11717.32 |
| 2400 | 511.75 | 1078.14 | 2599.95 | 10114.50 |
| 3500 | 413.10 | 944.00 | 2271.42 | 8582.30 |
| 4900 | 354.51 | 850.40 | 1995.34 | 7320.40 |
| 7000 | 313.01 | 771.86 | 1743.30 | 6098.66 |
| 10100 | 284.53 | 708.27 | 1534.00 | 4963.12 |
| 14400 | 265.86 | 655.16 | 1352.04 | 3993.29 |
| 20500 | 252.29 | 610.97 | 1203.18 | 3183.46 |
| 29300 | 241.95 | 574.59 | 1071.80 | 2506.22 |
| 41900 | 234.18 | 544.18 | 956.58 | 1962.19 |
| 59800 | 228.06 | 516.53 | 851.63 | 1531.37 |
| 85300 | 222.98 | 488.65 | 749.62 | 1190.80 |
| 122000 | 217.97 | 457.93 | 650.04 | 920.17 |
| 174000 | 212.54 | 422.51 | 553.03 | 709.85 |

TABLE 3

| | Phase of Impedance (degrees) | | | |
|---|---|---|---|---|
| Freq. (Hz) | Calibration | Columnar | High Grade | Squamous |
| 200 | 79.54 | 71.61 | 52.58 | 27.16 |
| 300 | 77.84 | 66.06 | 49.58 | 25.96 |
| 400 | 76.23 | 62.91 | 46.75 | 25.29 |
| 600 | 73.07 | 57.91 | 43.58 | 26.22 |
| 800 | 70.16 | 53.76 | 41.10 | 27.37 |
| 1200 | 64.90 | 47.86 | 38.03 | 29.52 |
| 1700 | 59.25 | 42.94 | 35.78 | 31.88 |
| 2400 | 52.74 | 38.41 | 33.88 | 34.94 |
| 3500 | 45.01 | 33.94 | 32.28 | 38.46 |
| 4900 | 38.12 | 30.46 | 31.48 | 41.80 |
| 7000 | 31.38 | 27.24 | 30.70 | 45.59 |
| 10100 | 25.46 | 24.41 | 30.15 | 49.36 |
| 14400 | 20.81 | 22.12 | 29.73 | 52.49 |
| 20500 | 17.23 | 20.35 | 29.78 | 55.27 |
| 29300 | 14.56 | 19.22 | 30.28 | 57.76 |
| 41900 | 12.75 | 18.91 | 31.45 | 59.93 |
| 59800 | 11.80 | 19.60 | 33.50 | 61.80 |
| 85300 | 11.70 | 21.47 | 36.38 | 63.46 |
| 122000 | 12.54 | 24.71 | 40.25 | 65.04 |
| 174000 | 14.44 | 29.33 | 44.85 | 66.69 |

We claim:

1. A method of tissue-type recognition, said method comprising the steps of:
   applying electrical signals to a tissue sample;
   measuring from the applied signals a magnitude of impedance of the tissue and corresponding phase sample at each of a plurality of frequencies;
   comparing at least the measured phase samples with phase information of known tissue types taken at said frequencies; and
   from said comparison, estimating to which of said known tissue-types said tissue sample corresponds.

2. A method according to claim 1 wherein said frequencies comprise at least two frequencies selected in the band from 3 kHz to 12 kHz.

3. A method according to claim 2 wherein said two frequencies are selected from the band from 5 kHz to 10 kHz.

4. A method according to claim 1 wherein said plurality of frequencies comprises two frequencies and said comparing comprises determining a ratio of the measured phase samples at said frequencies and comparing said ratio with corresponding known ratios determined from said phase information.

5. A method according to claim 1 wherein said comparing comprises determining a slope of a phase plot obtained from said measured phase samples and comparing said determined slope with corresponding known slopes from said phase information.

6. A method according to claim 1 further comprising, after said measuring and before said estimating, the further step of:
   comparing said measured magnitudes of impedance with impedance magnitude information of said known tissue-types taken at said frequencies.

7. A method according to claim 6 wherein said estimating comprises cross-referencing a comparison result from said measured phase samples with a comparison result obtained using said measured magnitudes of impedance.

8. A method according to claim 1 wherein said electrical signals are applied to the tissue sample via a plurality of electrodes arranged to detect a surface effect of the tissue sample.

9. A method according to claim 8 wherein said electrodes comprise a pair of electrodes each of which is contacted to the tissue sample.

10. A method according to claim 8 wherein said electrodes comprise at least three electrodes configured to contact the tissue sample.

11. A method according to claim 8 wherein said electrodes comprises a first plurality of electrodes operatively divisible into groups of a second (smaller) plurality of electrodes such that each group is operable as a bipolar electrode group for the stimulating and measuring of a response of the tissue sample to said signals.

12. A method according to claim 8 wherein said electrodes further comprise a reference electrode physically distanced from whilst conductively coupled to the tissue sample.

13. A method according to claim 8 wherein said applying comprises applying said signals simultaneously to a predetermined plurality of said electrodes whilst using a predetermined one of said electrodes as a reference electrode.

14. A method according to claim 8 further comprising characterising electrical properties of said electrodes using measurements from the applied signals.

15. A method according to claim 14 wherein said characterising comprises determining a double-layer capacitance of said electrodes.

16. A method according to claim 1 wherein said signals comprise pulses and said measurements comprise decay measurements.

17. A method according to claim 16 further comprising using impedance sweep data to provide correction factors for time domain analysis.

18. A method of determining a database for diagnosis of tissue types, said method comprising the steps of:
   (a) for each of a plurality of tissue samples,
      (i) identifying a known tissue type of said sample;
      (ii) taking at least phase measurements using electrical signals applied to said sample, said measurements comprising components at each of a plurality of frequencies;
   (b) arranging the phase measurements at each said frequency into a group associated with each said known tissue type;
   (c) processing the phase measurements in each said group to provide a processed phase value at each said frequency for each said tissue type; and
   (d) arranging the processed phase values as a database.

19. A method according to claim 18 wherein step (a)(i) comprises at least one of cytology, hystology, colposcopy, and traditional pathology.

20. A method according to claim 18 wherein the processing of step (c) comprises at least one of averaging and curve fitting.

21. A database for use in diagnosing tissue types, the database formed by the method steps of:
   (a) for each of a plurality of tissue samples,
      (i) identifying a known tissue type of said sample;
      (ii) taking at least phase measurements using electrical signals applied to said sample, said measurements comprising components at each of a plurality of frequencies,
   (b) arranging the phase measurements at each said frequency into a group associated with each said known tissue type;
   (c) processing the phase measurements in each said group to provide a processed phase value at each said frequency for each said tissue type; and
   (d) arranging the processed phase values as a database.

22. A method of estimating a known tissue-type for a tissue sample, said method comprising:
   (a) obtaining phase measurements at predetermined frequencies of said tissue sample;
   (b) comparing said phase measurements at said frequencies with average values obtained from a database according to claim 21; and
   (c) identifying a known tissue type having average phase values that best match said phase measurements at each of said frequencies.

23. A method of tissue-type recognition, said method comprising the steps of:
   applying electrical signals to a tissue sample at at least two frequencies from a range of frequencies;
   measuring from the applied signals, at each of said at least two frequencies, a magnitude of tissue impedance and a phase of tissue impedance;
   calculating a slope of phase versus frequency from said measured phases;
   comparing at least said slope with phase slope information of known tissue-types over said range of frequencies; and from said comparison, estimating which of said known tissue-types said tissue sample corresponds to.

24. A method according to claim 18 wherein said measurements are taken from said tissue sample in vivo.

25. Apparatus for tissue-type recognition, comprising:
   electrode means for applying electrical signals to a tissue sample;
   means for measuring from the applied signals a magnitude of impedance of the tissue and corresponding phase sample at each of a plurality of frequencies;
   means for comparing at least the measured phase samples with phase information of known tissue-types taken at said frequencies; and
   means for estimating, from said comparison, to which of said known tissue-types said tissue sample corresponds.

26. Apparatus according to claim 25 wherein said electrode means is selected from the group consisting of:
   a pair of electrodes, each of which is contacted to the tissue sample;
   at least three electrodes configured to contact the tissue sample; and
   a first plurality of electrodes operatively divisible into groups of a second (smaller) plurality of electrodes such that each group is operable as a bipolar electrode group for the stimulating and measuring of a response of the tissue sample to said signals.

27. Apparatus for tissue-type recognition, comprising:
   electrode means for applying electrical signals to a tissue sample at at least two frequencies from a range of frequencies;
   means for measuring from the applied signals, at each of said at least two frequencies, a magnitude of tissue impedance and a phase of tissue impedance;
   means for calculating a slope of phase versus frequency from said measured phases;
   means for comparing at least said slope with phase slope information of known tissue-types over said range of frequencies; and
   means for estimating, from said comparison, which of said known tissue-types said tissue sample corresponds to.

28. A system for tissue type recognition, said system comprising:
   a database of tissue types, wherein the database is produced by the steps of
      (a) for each of a plurality of tissue samples,
         (i) identifying a known tissue type of said sample;
         (ii) taking at least phase measurements using electrical signals applied to said sample, said measurements comprising components at each of a plurality of frequencies;
      (b) arranging the phase measurements at each said frequency into a group associated with each said known tissue type;
      (c) processing the phase measurements in each said group to provide a processed phase value at each said frequency for each said tissue type; and
      (d) arranging the processed phase values as a database; and
   electrode means for applying electrical signals to a tissue sample;
   means for measuring from the applied signals a magnitude of impedance of the tissue and corresponding phase sample at each of a plurality of frequencies;
   means for comparing at least the measured phase samples with said database; and
   means for estimating, from said comparison, to which of said known tissue-types said tissue sample corresponds.

29. A method of compensating for production variations in an electrode intended for use in determining properties of living tissue, the method comprising the steps of:
   measuring time constants of a voltage decay curve and a current decay curve with said electrode in a reference medium;
   estimating a capacitance of said electrode from said time constants;
   calculating a correction factor for said electrode based on said estimated capacitance; and
   applying said correction factor to measurements obtained from said living tissue using said electrode.

* * * * *